US008663955B2

(12) United States Patent
Ruedinger

(10) Patent No.: US 8,663,955 B2
(45) Date of Patent: Mar. 4, 2014

(54) METHOD FOR PRODUCING CARBOXYLIC ACIDS HAVING 1-3 CARBON ATOMS FROM RENEWABLE RESOURCES

(75) Inventor: Christoph Ruedinger, Starnberg (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 13/522,404

(22) PCT Filed: Jan. 27, 2011

(86) PCT No.: PCT/EP2011/051102
§ 371 (c)(1),
(2), (4) Date: Jul. 16, 2012

(87) PCT Pub. No.: WO2011/092228
PCT Pub. Date: Aug. 4, 2011

(65) Prior Publication Data
US 2012/0288908 A1 Nov. 15, 2012

(30) Foreign Application Priority Data

Jan. 29, 2010 (DE) .......................... 10 2010 001 399

(51) Int. Cl.
*C12P 7/54* (2006.01)
(52) U.S. Cl.
USPC ........................................................ 435/140
(58) Field of Classification Search
None
See application file for complete search history.

(56) References Cited

U.S. PATENT DOCUMENTS

| 4,350,830 | A | 9/1982 | Childress et al. |
|---|---|---|---|
| 4,415,752 | A | 11/1983 | Decker et al. |
| 4,434,031 | A | 2/1984 | Horowitz et al. |
| 4,620,035 | A | 10/1986 | Krabetz et al. |
| 5,162,578 | A | 11/1992 | McCain, Jr. et al. |
| 5,300,682 | A | 4/1994 | Blum et al. |
| 6,060,421 | A | 5/2000 | Karim et al. |
| 6,274,763 | B1 | 8/2001 | Ruedinger et al. |
| 6,274,765 | B1 | 8/2001 | Borchert et al. |
| 6,281,385 | B1 | 8/2001 | Ruedinger et al. |
| 6,310,241 | B1 | 10/2001 | Karim et al. |
| 6,320,075 | B1 * | 11/2001 | Ruedinger et al. ............ 562/549 |
| 6,399,816 | B1 | 6/2002 | Borchert et al. |
| 6,429,331 | B1 | 8/2002 | Ruedinger et al. |
| 6,692,706 | B2 | 2/2004 | Ruedinger et al. |
| 6,695,952 | B1 | 2/2004 | Ruedinger et al. |
| 6,793,777 | B1 | 9/2004 | Ruedinger et al. |
| 6,884,909 | B2 | 4/2005 | Ruedinger et al. |
| 7,642,214 | B2 | 1/2010 | Kobayashi et al. |
| 2005/0085678 | A1 | 4/2005 | Lopez Nieto et al. |
| 2006/0128988 | A1 | 6/2006 | Brazdil et al. |
| 2009/0215152 | A1 | 8/2009 | Xu et al. |

FOREIGN PATENT DOCUMENTS

| EP | 0294846 A2 | 12/1988 |
|---|---|---|
| JP | 57-54287 A | 3/1982 |
| JP | 64-63541 A | 3/1989 |
| WO | 03033138 A1 | 4/2003 |
| WO | 2006053480 A1 | 5/2006 |

OTHER PUBLICATIONS

Celinska et al., Biotechnological production of 2,3-butanediol—Current state and prospects, Biotechnology Advances 27 (2009) 715-725.*
Aden, et al., "Ligonocellulosic Biomass to Ethanol Process Design and Economics Utilizing Co-current Dilute Acid Prehydrolysis and Enzymatic Hydrolysis for Corn Stover", Technical Report, Jun. 2002, 154 pages, NREL/TP-510-32438, National Renewable Energy Laboratory, Golden, Colorado.
Cheung, et al., "Acetic Acid", Ullmann's Encyclopedia of Industrial Chemistry, pp. 1-30 (Wiley-VCH; 2000).
Kaneda et al., "MoO2(acac)2 Complex as a Reagent for Oxidative Cleavage of vic-Diols", Chemistry Letters, pp. 1295-1296 (1988).
Nomiya, et al., "Photo-oxidations of Acetoin and Biacetyl Catalyzed by Tetrabutylammonium Decatungstate(4-) in Acetonitrile under Excess of Oxygen", Journal of the Chemical Society, pp. 961-962 (1987).
Prati, et al., "Stepwise Oxidation of 1,2-diols Resulting from Molecular Oxygen Activation by Copper" Journal of Molecular Catalysis A: Chemical, vol. 110, pp. 221-226 (1996).
Syu, "Biological Production of 2,3-butanediol", Appl. Microbiol. Biotechnol., vol. 55, pp. 10-18 (2001).
Venturello, et al., "Oxidative Cleavage of 1,2-Diols to Carboxylic Acids by Hydrogen Peroxide", Journal of Organic Chemistry, vol. 51, pp. 1599-1602 (1986).
International Search Report for PCT/EP2011/051102 dated May 13, 2011.
International Preliminary Report of Patentability relating to PCT/EP2011/051102.

* cited by examiner

*Primary Examiner* — Suzanne M Noakes
*Assistant Examiner* — Stephen Chong
(74) *Attorney, Agent, or Firm* — Caesar, Rivise, Bernstein, Cohen & Pokotilow, Ltd.

(57) ABSTRACT

The invention relates to a method for producing carboxylic acids having 1-3 carbon atoms, characterized in that 2,3-butanediol and/or acetoin are reacted to form carboxylic acids having 1-3 carbon atoms.

14 Claims, 2 Drawing Sheets

METHOD FOR PRODUCING CARBOXYLIC ACIDS HAVING 1-3 CARBON ATOMS FROM RENEWABLE RESOURCES

BACKGROUND OF THE INVENTION

The invention relates to methods for producing carboxylic acids having 1-3 carbon atoms, specifically acetic acid from 2,3-butanediol and/or acetoin.

Acetic acid can be produced on an industrial scale by oxidation of acetaldehyde, oxidation of ethylene, oxidation of ethane and oxidation of other hydrocarbons and also carbonylation of methanol (Ullmans Encyclopedia of Industrial Chemistry, 2000, Vol. 1, "Acetic Acid", pp. 151-164).

Acetic acid can also be obtained on the basis of renewable raw materials by oxidative fermentation of ethanol obtained from vegetable raw materials (Ullmans Encyclopedia of Industrial Chemistry, 2000, Vol. 1, "Acetic Acid", pp. 164-165). But this method is economically uncompetitive with the above-mentioned methods, which are based on fossil raw materials.

The invention has for its object to provide an inexpensive method for producing carboxylic acids having 1-3 carbon atoms, specifically acetic acid, which is also able to use renewable raw materials as starting basis.

DESCRIPTION OF THE INVENTION

This object is achieved by a method that is characterized in that 2,3-butanediol and/or acetoin are converted to a carboxylic acid having 1-3 carbon atoms.

It is preferable for 2,3-butanediol and/or acetoin to be converted to acetic acid by chemical oxidation.

The oxidation of 2,3-butanediol and acetoin is preferably effected with oxygen or an oxygen-containing gas. It is preferable for a homogeneously or heterogeneously catalyzed oxidation to be concerned, and the heterogeneously catalyzed oxidation is particularly preferred. The oxidation can take place in the liquid phase or in the gas phase.

It is particularly preferable for 2,3-butanediol and/or acetoin to be used as mixture obtained from carbohydrate-containing raw materials via a fermentation.

The fermentative production of 2,3-butanediol and acetoin is known (e.g., Appl. Microbiol. Biotechnol.; (2001); 55; 10-18 and WO 2006/053480). Any carbohydrate-containing raw material can serve as fermentation reactant. Preference is given to fermentable, carbohydrate-containing fractions from the destructurization of lignocellulosics (e.g., "Lignocellulosic Biomass to Ethanol Process Design and Economics Utilizing Co-Current Dilute Acid Prehydrolysis and Enzymatic Hydrolysis for Corn Stover"; A. Aden, M. Ruth, K. Ibsen, J. Jechura, K. Neeves, J. Sheehan, and B. Wallace; National Renewable Energy Laboratory L. Montague, A. Slayton, and J. Lukas; Harris Group; Seattle, Wash.; National Renewable Energy Laboratory; Contract No. DE-AC36-99-GO10337; June 2002.NREL/TP-510-32438).

The carbohydrate-containing raw materials preferably contain mono-, di- and oligosaccharides, such as sucrose, maltose and also C6 and/or C5 simple sugars. It is particularly preferable for the C6 and C5 sugars to be glucose, xylose or arabinose.

The carbohydrate-containing raw materials are initially converted in one of the known fermentation processes for the production of 2,3-butanediol into a fermentation mixture containing compounds having 2 to 5 carbon atoms. It is particularly preferable for these compounds to be stereoisomers of 2,3-butanediol (S,S; R,R; or meso) or acetoin (3-hydroxy-2-butanone, R- or S-form).

Typical coproducts generated in the fermentative production of 2,3-butanediol and therefore likewise possibly present in the fermentation mixture are acetoin, ethanol and acetic acid. Since these compounds are likewise intermediates in the oxidation to acetic acid, the as-obtained fermentation mixture—without further removal of 2,3-butanediol—can be used in the chemical oxidation process in admixture with 2,3-butanediol to increase the yield of acetic acid.

Preferably, the compounds are present in the fermentation mixture, i.e., the mixture obtained from the fermentation, as aqueous solution having a water concentration of 1-90 wt % and more preferably having a water content between 40-80 wt %.

It is particularly preferable for the fermentation mixture, i.e., the mixture obtained from the fermentation, to be partially purified before use in the method of the present invention. The partial purification removes some of the water content and of the non-vaporizable impurities (cells, salts, polymers, proteins, sugars). It is preferable to remove 10-90 wt % of the water content and more than 99% of the impurities mentioned.

The fermentation liquor, i.e., the liquor obtained from the fermentation, is more preferably treated by decanting, centrifugation, filtration, microfiltration, nanofiltration, ultrafiltration, reverse osmosis, membrane permeation, pervaporation, simple distillation, rectification, extraction, crystallization to produce an aqueous mixture containing 2,3-butanediol and acetoin as main components as well as customary fermentation by-products. Customary fermentation by-products are preferably alcohols such as, for example, ethanol and organic acids such as pyruvic acid, lactic acid and acetic acid.

Preferably, the concentration of customary fermentation by-products in the mixture is each individually below wt % and collectively below 60 wt % of the total amount of 2,3-butanediol and acetoin present in the aqueous solution.

This 2,3-butanediol- and acetoin-containing fermentation mixture is the particularly preferred starting material for the method of the present invention.

The oxidation of 2,3-butanediol and/or acetoin is preferably carried out in a reactor which is suitable for performing oxidation reactions and which is capable of removing the high heat of reaction without unduly heating the reaction mixture. The reactor is preferably a stirred tank reactor, a bubble column reactor or a tubular/tube-bundle reactor. Processes suitable in principle for performing the oxidation reaction and the purification and recovery of chemically pure acetic acid are described inter alia in U.S. Pat. No. 6,320,075 B1, U.S. Pat. No. 6,692,706 B2, U.S. Pat. No. 6,429,331, U.S. Pat. No. 6,884,909 B2, U.S. Pat. Nos. 6,793,777 B1 and 6,695,952 B1.

The reaction temperature for the oxidation is preferably in the range from 100° C. to 400° C., more preferably in the range from 150° C. to 300° C. and even more preferably in the range from 180° C. to 290° C.

The oxidation is preferably effected at pressures between $1.2*10^5$ and $51*10^5$ Pa, more preferably between $3*10^5$ and $21*10^5$ Pa and even more preferably between $4*10^5$ and $12*10^5$ Pa.

Any catalyst described for the partial oxidation of hydrocarbons is suitable. Preferably, the catalyst contains one or more of the elements vanadium, molybdenum, antimony, niobium, titanium and precious metals. The precious metal fraction in the catalyst preferably contains one or more of the elements Ru, Rh, Pd, Pt. Preference is given to mixed oxide catalysts and particular preference is given to catalysts that contain vanadium oxides.

Suitable catalysts are described inter alia in: U.S. Pat. No. 4,350,830, U.S. Pat. No. 4,415,752, U.S. Pat. No. 4,620,035, U.S. Pat. No. 5,162,578, U.S. Pat. No. 5,300,682, U.S. Pat. No. 6,060,421, U.S. Pat. No. 6,274,763 B1, U.S. Pat. No. 6,274,765 B1, U.S. Pat. No. 6,310,241 B1, U.S. Pat. No. 6,399,816, WO 03/033138 A1, US 2005/0085678 A1, US 2006/0128988 A1, U.S. Pat. No. 7,642,214 B2, U.S. Pat. No. 6,429,331 B1 column 7, lines 1-33, U.S. Pat. No. 6,320,075 B1, U.S. Pat. No. 6,884,909 B2.

The oxidation of the present invention can be carried out as a continuous operation or as an intermittent operation; that is, reactor feed rate and composition can be constant, or reactor feed rate and/or composition can vary over time.

The mixture of materials which is to be made to react is preferably reacted over a catalyst in a fixed bed, for example in a tube-bundle reactor or a tray reactor, or in a moving/fluidized bed.

Preference is given to cooled tube-bundle reactors with a fixed catalyst bed. Particular preference is given to embodiments where individual tubes arranged into tube-bundle form have tube inside diameters of 10 mm to 50 mm and a tube length of 1 m to 6 m.

Average flow velocity in the reaction tubes, based on the unpacked tube, is between 0.1 m/s and 10 m/s, preferably between 0.3 m/s and 5 m/s and more preferably in the range from 0.5 to 3 m/s.

The reaction tubes can be packed with a catalyst differing in composition, shape and size. The packing may preferably have been introduced into the reaction tubes in an axially homogeneous or zonally varied manner. In a zonally varied packing, each zone preferably contains a randomly diluted or mixed catalyst.

The oxygen source necessary for gas phase oxidation is an oxygen-containing gas. The oxygen-containing gas used can be, for example, air, optionally after mechanical cleaning, preferably oxygen-enriched air and more preferably pure oxygen. The method of the present invention, however, may also utilize in addition an inert gas, preferably nitrogen and/or argon in an amount of 0 to 25 vol %.

The oxygen content of the gas stream supplied to the reactor is preferably in the range from 1 to 35 vol %, more preferably in the range from 3 to 20 vol % and especially in the range from 4 to 12 vol %, preference being given to embodiments wherein the gas mixture is non-incentive (within the meaning of DIN EN 1839 or ASTM E681) at the reactor inlet under conditions (temperature, partial pressures of components) prevailing there.

The volume fraction of water vapor in the gas stream supplied to the reactor is generally in the range from 0 to 80 vol %, preferably in the range from 1 to 40 vol % and more preferably in the range from 3 to 30 vol % of water vapor.

The fraction of 2,3-butanediol and/or acetoin in the gas stream, as measured at the reactor entry of the gas stream supplied to the reactor, is generally in the range from 0.1 to 20 vol %, preferably in the range from 0.5 to 10 vol % and more preferably in the range from 1 to 8.0 vol %.

In a preferred embodiment of the invention, the method of the present invention is operated as a recycle process wherein a portion of the gas mixture leaving the reactor is returned to the reactor inlet, optionally after removing various materials from this mixture. The reaction gas recycle in this embodiment can take the form of some of the organic acids formed in the course of the gas phase oxidation being removed from the reaction exit gas such that the acid fraction in the recycled portion of the reaction exit gas is reduced to 0.01 to 8 vol %.

In the case of methods involving gas recycle, the proportion of carbon oxides and further reaction by-products in the reactor inlet gas depends on reaction conduct and acid removal, and is generally in the range from 1 to 99 vol %, preferably in the range from 20 to 95 vol % and more preferably in the range from 50 to 92 vol %. The vol % proportions of the individual constituents of the reactor inlet gas sum to 100 vol % in each case.

As apparatus for conducting the oxidation of the present invention, it is generally possible to use apparatuses in which the gas makes a single pass through the reactor and recycle processes. In the case of recycle processes, the preference is for apparatuses in which the recirculated gas stream has removed from it high boilers (organic acids and compounds which under the separation conditions chosen have the same vapor pressure as acetic acid or higher vapor pressure than acetic acid), especially acetic acid, preferentially over the lower boilers (compounds which under the separation conditions chosen have a lower vapor pressure than acetic acid; especially water, acetaldehyde, CO, $CO_2$, ethanol, $O_2$, and ethyl acetate, 2-butanone, methyl acetate, ethyl formate, methyl formate, ethylene).

An aqueous crude acid containing the oxidation products is preferably removed from the gas mixture leaving the reactor (i.e., from the reactor outlet gas) using a countercurrent scrub, a cocurrent scrub, a cross-stream scrub, quench cooling, partial condensation or a combination of these methods. Further details concerning preferred embodiments are described in U.S. Pat. No. 6,320,075 B1, whose relevant disclosures (column 2 line 28 to column 4 line 21 and column 7 line 13 to column 8 line 6) are hereby incorporated by reference.

Preferably, the crude acid is removed from the reactor outlet gas via a countercurrent scrub. In a particularly advantageous embodiment of the invention, the reaction gas recycle is configured such that the reactor outlet gas has some of the organic acids formed in the course of the gas phase oxidation, preferably acetic acid, removed from it via a partial condenser or a countercurrent scrub with a suitable solvent, preferably water. To perform this separation, the partial pressure of acetic acid remains low at the reactor inlet while further-convertible by-products, such as acetaldehyde, ethyl acetate, methyl acetate, ethyl formate, methyl formate, etc very largely remain in the cycle gas and are returned back to the reactor inlet.

In one embodiment, one portion of the reactor outlet gas has generally from 20 to 99.8 wt % and preferably from 80 to 99.5 wt % of the acid fraction removed from it and then the acid-depleted portion of the gas stream is returned back to the reactor inlet. The untreated portion of the reactor outlet gas is discarded and can be burned for example. The proportion of untreated reactor outlet gas depends on how much carbon oxide $CO_x$ has been formed, since this has to be removed via this bleed stream. It can subsequently be disposed of via incineration for example.

In another embodiment, the entire reactor outlet gas has its acid fraction reduced wholly or partly, preferably by from 20 to 99.8 wt % and more preferably by from 80 to 99.5 wt % and a portion of the acid-depleted gas mixture is returned to the reactor inlet. This embodiment is particularly preferred.

The mass flow of recycled gas is generally between 1 and 100 times the mass flow of fresh feed (aqueous solution containing 2,3-butanediol or acetoin and oxygen), preferably between 2 times and 20 times and more preferably between 3 times to 9 times.

The water vapor content of the gas stream leaving the absorber is preferably fixed via the temperature at the absorber outlet and the operating pressure. This temperature is generally fixed via the heat quantity removed from the absorber and the rate and temperature of the scrub water stream, and is preferably in the range from 50° C. to 200° C. The residual acid content of the gas stream leaving the absorber is preferably fixed via pressure and temperature, the number of theoretical plates of the absorber and the absorbent (water) feed rate. The process is preferably carried out such that the countercurrent scrub reduces the residual acid concentration of the gas stream returned back into the reactor to from 0.01 to 12 vol %, preferably to from 0.1 to 8 vol % and more preferably to 0.35-1.4 vol %.

The removed crude acid is preferably dewatered and purified using customary methods, such as liquid-liquid extraction, extractive rectification, rectification, azeotropic rectification, crystallization and membrane separation. The low boilers (vapor pressure<vapor pressure of target product, preferably acetic acid) removed before any further separation of the crude acid into its pure substances can likewise be wholly or partly returned to the inlet of the reactor for oxidation of 2,3-butanediol, alone or together with low boilers from the purifying and concentrating operations.

Of particular suitability for working up the dilute crude acid are the cost-optimized processes described in U.S. Pat. No. 6,793,777 B1 (column 2 line 38 to column 7 line 19) and U.S. Pat. No. 6,695,952 B1 (column 2 line 39 to column 8 line 49), whose relevant disclosures are hereby incorporated herein by reference.

When acetic acid concentration in the crude acid is above 50 wt %, processes having simpler apparatus requirements, such as azeotropic rectification, are better value for money for the dewatering.

The water obtained in concentrating and purifying the crude acid can be partly fed back into the countercurrent absorption, optionally following a chemical and/or physical treatment. Since there is an excess of water in the whole process and, in addition to the extra water added, more water is formed by the oxidation process, recycled water from the acid-concentrating stage can at a maximum replace all the extra scrub water added at the absorber head. The excess water, which still contains very low levels of acetic acid and other organic acids, can readily be disposed of via a biological water treatment plant.

BRIEF DESCRIPTION OF THE DRAWINGS

The invention will be described in conjunction with the following drawings in which like reference numerals designate like elements and wherein:

FIG. 1a describes in schematic depiction an apparatus for producing acetic acid by gas phase oxidation of 2,3-butanediol and/or acetoin using the method of the present invention: A mixing zone (5) mixes oxygen (15) with the recycled gas stream (4) and feeds the mixture to the tube-bundle reactor (10). The reactor outlet gas (8) leaving the reactor passes through a gas/gas heat exchanger (2) to cool it down and leaves the heat exchanger (2) as a precooled reaction gas (18). The precooled reaction gas (18) is used in the feed vaporizer (1) to heat the liquid reactant stream (14), which is vaporized therein. Additional external heating may be needed for the feed vaporizer (1).

Figure 1A:
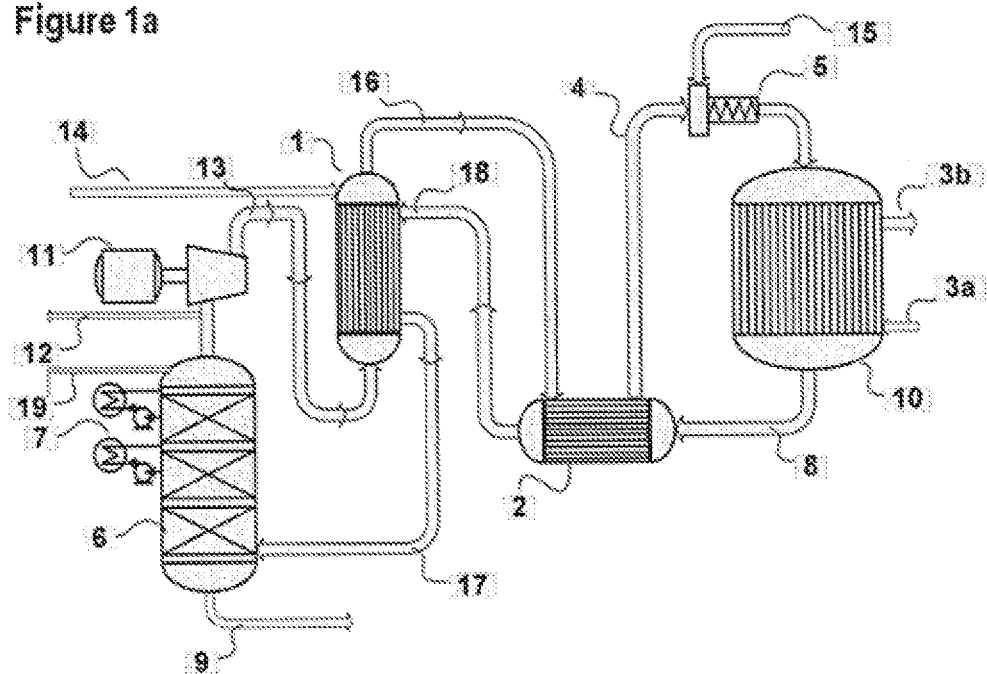
FIG. 1a shows a schematic depiction of an embodiment of an apparatus for producing acetic acid by gas phase oxidation of 2,3-butanediol and/or acetoin using the method of the present invention.

Thereafter, the reaction gas passes via a line (17) into an absorption column (6) which is equipped with one or more column coolers (7). A solvent, preferably water, is passed in at the uppermost column tray via a pipework line (19). In this absorption column, the crude acid is removed via countercurrent scrubbing and fed via a pipe (9) to the further workup stage. The remaining reaction gas is fed via a recycle gas compressor (11) to the feed vaporizer (1), where it is mixed with the vaporized reactant stream (14) and fed as recycled gas stream (16) to the gas/gas heat exchanger (2), where it is heated by the reactor exit gas (8) and as recycled gas stream (4) is again mixed with oxygen (15) in the mixing zone (5) and fed to the tube-bundle reactor (10).

The tube-bundle reactor (10) is cooled via a cooling circuit (3a steam condensate in, 3b steam out).

Figure 1B:
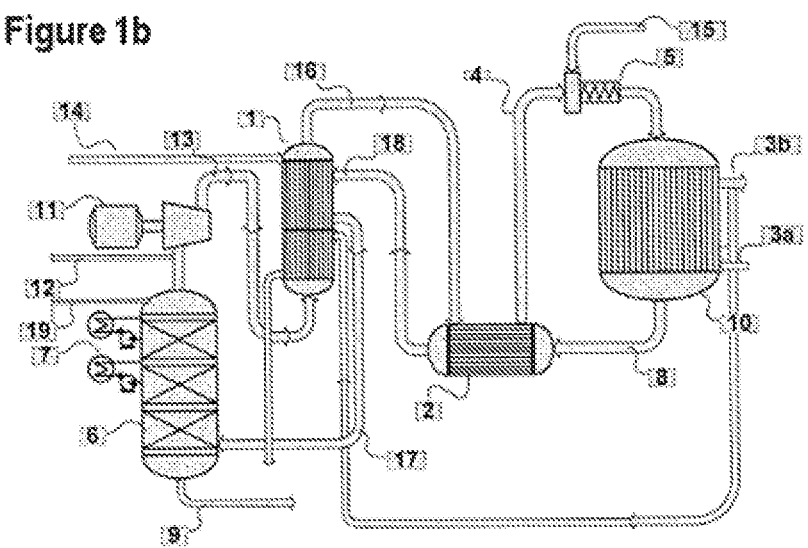
FIG. 1b shows a schematic depiction of another embodiment of an apparatus for producing acetic acid by gas phase oxidation of 2,3-butanediol and/or acetoin using the method of the present invention, wherein the feed vaporizer is additionally heated with steam.

FIG. 1b shows a version of the method according to the present invention wherein the feed vaporizer (1) is additionally heated with steam (3b).

In another possible embodiment for the apparatus and method, the reactant stream (14) is separately vaporized and then admixed in vapor form to the recycle gas stream upstream of where the oxygen is mixed in (15 & 5). When the vaporization and mixing with the recycle gas stream is carried out in a conjoint device (1), configured as vaporizer for the reactant stream (14) and suitable for mixing this vapor with the recycle gas stream in the manner, for example, of a falling film vaporizer through which the recycle gas stream flows, it may be sensible to heat this device additionally to the energy input via the recycle gas streams. Line (12) is used to remove an off-gas stream to maintain steady-state conditions in the reaction circuit. This off-gas stream can be cooled down in an off-gas cooler, in which case the condensate produced is discarded or, preferably, fed back into the reaction circuit in place of the feed vaporizer (1). The recycle gas stream is incidentally the gas stream which circulates in the recycle gas plant, i.e., being pumped by the recycle gas compressor (11) through all devices of the circuit 1→2→5→10→2→1→6→1.

Figure 2:
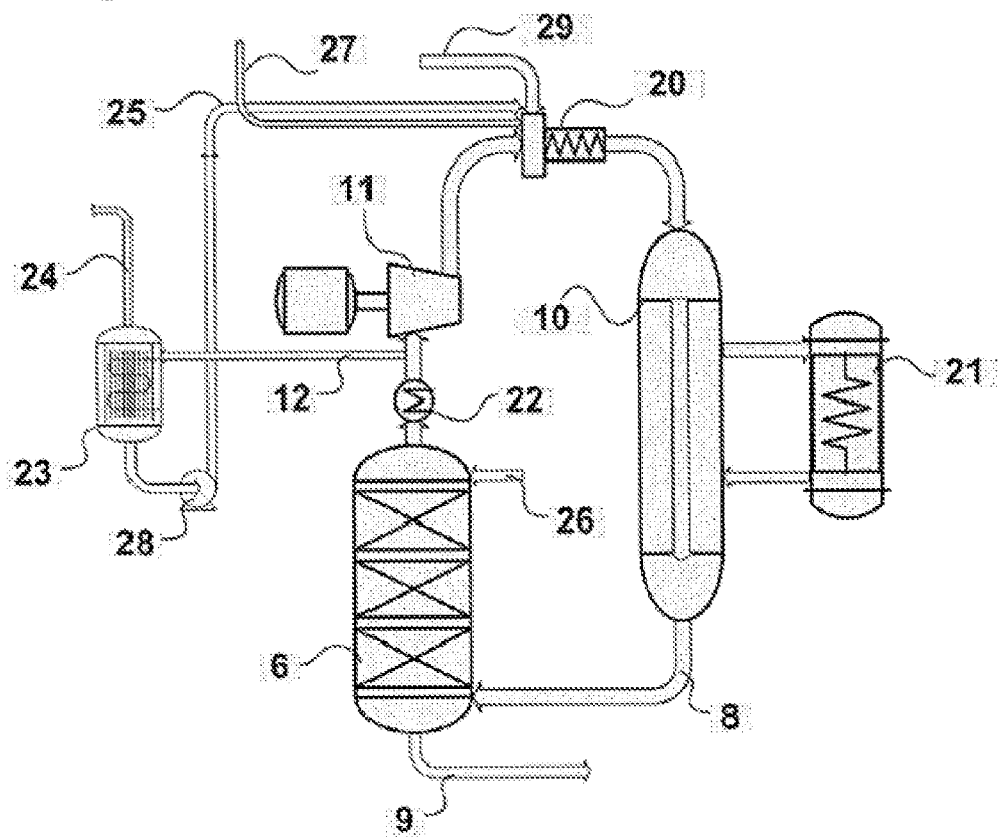
FIG. 2 shows a schematic depiction of the apparatus used in the examples to produce acetic acid by gas phase oxidation of 2,3-butanediol and/or acetoin.

FIG. 2 shows the apparatus used in the examples.

The examples which follow serve to further elucidate the invention.

The selectivity [in mol %] was computed as follows:
acetic acid selectivity based on 2,3-butanediol or acetoin conversion (mol %)

=>((mol/h of acetic acid in crude acid))/(mol/h of converted C4–reactant/2)*100 formic acid selectivity based on 2,3-butanediol or acetoin conversion (mol %)

=>((mol/h of formic acid in crude acid)/4)/(mol/h of converted C4–reactant)*100

Exemplified Catalyst:
Catalyst I (Examples 1 to 14):

The catalytically active mass is prepared as described in Example 19 of U.S. Pat. No. 6,281,385 B1. The active mass consists of oxides of titanium, vanadium and antimony of the empirical formula $Ti_aV_bSb_cO_d$ (a:10; b:1; c:1; d:24). It was used in the form of extruded and cut rings dimensioned 5 mm outside diameter*2 mm inside diameter*5 mm height.

Catalyst II (Examples 15 and 16):

The catalytically active mass was prepared as described in Preparation Procedure A of U.S. Pat. No. 6,310,241 B1. The active mass consists of oxides of palladium, vanadium, molybdenum and niobium of the empirical formula $Pd_aV_b\text{-}Mo_cNb_dO_e$ (a:0.0067; b:1; c:2; d:0.16; e:9). It was used in the form of extruded and cut rings dimensioned 5 mm outside diameter*2 mm inside diameter*5 mm height.

Catalyst III (Examples 17 to 20):

The catalytically active mass was prepared as described in Example 19 of U.S. Pat. No. 6,281,385 B1. The active mass consists of oxides of titanium, vanadium and molybdenum of the empirical formula $Ti_aV_bMo_cO_d$ (a:10; b:1; c:0.2; d:23). It was used in the form of extruded and cut rings dimensioned 5 mm outside diameter*2 mm inside diameter*5 mm height.

The experiments were carried out in an apparatus corresponding to FIG. 2 with a one-tube reactor (10) with circulating oil cooling (21) with 15 mm inside diameter for the reaction tube and an absorption column (6) with structured packing, an inside diameter of 43 mm and a packing height of 3240 mm with thermostated head-part condenser (22) as column cooler. The liquid reactant stream (27) is vaporized in the heated vaporizing and mixing means (20) and mixed therein with the recycle gas stream together with the oxygen (29). The reactor exit gas leaving the reactor (10) via line (8) is scrubbed in the absorption column (6). The scrubbing liquid is added via line (26) at the top of the column. The temperature at the top of the column is set via the column top cooler (22). The gas leaving the column top cooler is pumped back to the heated vaporizing and mixing means (20) via the compressor (11). The gas mixture leaving the absorber (6) has removed from it an off-gas stream (12) which is cooled down in the off-gas condenser (23). The uncondensable constituents, predominantly carbon oxides, leave the reaction system via line (24) after letdown, while condensable constituents, predominantly water, return via the pump (28) and the line (25) into the heated vaporizing and mixing means (20) for vaporization and mixing with the recycle gas stream. Line (9) is used to withdraw the product acetic acid via the aqueous crude acid at the base of the absorption column (6), and remove it from the reaction cycle.

EXAMPLE 1

Oxidation of 2,3-butanediol

Catalyst I was installed in a reactor having a reaction tube inside diameter of 15 mm to a fill level height of 1310 mm. The oxygen content at reactor entry was automatically controlled to 4.5 vol % by addition of pure oxygen at the point of reactor entry. The reaction feed used amounted to 97.9 g of a stereoisomer mixture having the following composition: about 15 wt % of R,R-2,3-butanediol, about 15 wt % of S,S-2,3-butanediol, about 70 wt % of meso-2,3-butanediol. This stereoisomer mixture is hereinafter referred to as 2,3-butanediol. For absorption, 498 g/h of water were fed in recycle gas flow direction at a point directly upstream of the column head cooler of the absorption column. The recycle gas flow was adjusted such that the reactor reached a recycle gas flow of 7000 g/h in the stable state. The reactor was operated at $10.9*10^5$ Pa pressure and 180.0° C. coolant temperature.

Acid separation from the reaction gas was effected by absorption in a countercurrent absorber with structured packing, an inside diameter of 43 mm and a packing height of 3240 mm at a head temperature of 130° C. for the absorber.

A 2,3-butanediol conversion of 100% was achieved under these conditions. Acetic acid selectivity based on conversion was 82 mol % and formic acid selectivity based on conversion was 6 mol %. Volume-specific acetic acid productivity was 453 g/lh. The crude acid contained 80 wt % of water.

EXAMPLES 2-9

Examples 2 to 9 were carried out similarly to Example 1 except for the differences reported in Table 1.

EXAMPLE 10

Oxidation of acetoin (3-hydroxy-2-butanone): Catalyst I was installed in a reactor having a reaction tube inside diameter of 15 mm to a fill level height of 1310 mm. The oxygen content at reactor entry was automatically controlled to 4.54 vol % by addition of pure oxygen at the point of reactor entry. The reaction feed added amounted to 233 g/h of an aqueous solution of a racemate (equimolar mixture of R- and S-form) of acetoin (3-hydroxy-2-butanone)), hereinafter referred to as acetoin, corresponding to 58.2 g/h of acetoin. For absorption, 218 g/h of water were fed in recycle gas flow direction at a point directly upstream of the column head cooler of the absorption column. The recycle gas flow was adjusted such that the reactor reached a recycle gas flow of 6950 g/h in the stable state. The reactor was operated at $11*10^5$ Pa pressure and 208° C. coolant temperature.

Acid separation from the reaction gas was effected by absorption in a countercurrent absorber with structured packing, an inside diameter of 43 mm and a packing height of 3240 mm at a head temperature of 130° C. for the absorber.

An acetoin conversion of 100% was achieved under these conditions. Acetic acid selectivity based on conversion was 80 mol % and formic acid selectivity based on conversion was 2.4 mol %. Volume-specific acetic acid productivity was 270 g/lh. The crude acid contained 87 wt % of water.

EXAMPLES 11-14

Examples 11 to 14 were carried out similarly to Example 10, except for the differences reported in Table 2.

EXAMPLE 15

Oxidation of 2,3-butanediol

Catalyst II was installed in a reactor having a reaction tube inside diameter of 15 mm to a fill level height of 1300 mm. The oxygen content at reactor entry was automatically controlled to 4.5 vol % by addition of pure oxygen at the point of reactor entry. The reaction feed used amounted to 105 g of a stereoisomer mixture having the following composition: about 15 wt % of R,R-2,3-butanediol, about 15 wt % of S,S-2,3-butanediol, about 70 wt % of meso-2,3-butanediol. This stereoisomer mixture is hereinafter referred to as 2,3-butanediol. For absorption, 520 g/h of water were fed in recycle gas flow direction at a point directly upstream of the column head cooler of the absorption column. The recycle gas flow was adjusted such that the reactor reached a recycle gas flow of 6000 g/h in the stable state. The reactor was operated at $10.9*10^5$ Pa pressure and 243.5° C. coolant temperature.

Acid separation from the reaction gas was effected by absorption in a countercurrent absorber with structured packing, an inside diameter of 43 mm and a packing height of 3240 mm at a head temperature of 130° C. for the absorber.

A 2,3-butanediol conversion of 100% was achieved under these conditions. Acetic acid selectivity based on conversion was 92 mol % and formic acid selectivity based on conversion was 1 mol %. Volume-specific acetic acid productivity was 549 g/lh. The crude acid contained 80 wt % of water.

EXAMPLE 16

Example 16 was carried out similarly to Example 15, except for the differences reported in Table 3.

EXAMPLE 17

Oxidation of 2,3-butanediol

Catalyst III was installed in a reactor having a reaction tube inside diameter of 15 mm to a fill level height of 1000 mm. The oxygen content at reactor entry was automatically controlled to 4.5 vol % by addition of pure oxygen at the point of reactor entry. The reaction feed used amounted to 99.7 g of a stereoisomer mixture having the following composition: about 15 wt % of R,R-2,3-butanediol, about 15 wt % of S,S-2,3-butanediol, about 70 wt % of meso-2,3-butanediol. This stereoisomer mixture is hereinafter referred to as 2,3-butanediol. For absorption, 497 g/h of water were fed in recycle gas flow direction at a point directly upstream of the column head cooler of the absorption column. The recycle gas flow was adjusted such that the reactor reached a recycle gas flow of 6 kg/h in the stable state. The reactor was operated at $11*10^5$ Pa pressure and 180.0° C. coolant temperature.

Acid separation from the reaction gas was effected by absorption in a countercurrent absorber with structured packing, an inside diameter of 43 mm and a packing height of 3240 mm at a head temperature of 130° C. for the absorber.

A 2,3-butanediol conversion of 100% was achieved under these conditions. Acetic acid selectivity based on conversion was 84.5 mol % and formic acid selectivity based on conversion was 5.4 mol %. Volume-specific acetic acid productivity was about 600 g/lh. The crude acid contained 80 wt % of water.

EXAMPLE 18

Example 18 was carried out similarly to Example 17, except for the differences reported in Table 4.

EXAMPLE 19

Oxidation of 2,3-butanediol/acetoin (3-hydroxy-2-butanone) mixtures

Catalyst III was installed in a reactor having a reaction tube inside diameter of 15 mm to a fill level height of 1000 mm. The oxygen content at reactor entry was automatically controlled to 4.52 vol % by addition of pure oxygen at the point of reactor entry. The reaction feed added was a mixture of 10 g/h of a racemate (equimolar mixture of R- and S-form) of acetoin (3-hydroxy-2-butanone), hereinafter referred to as acetoin, and 89.6 g/h of a stereoisomer mixture having the following composition: about 15 wt % of R,R-2,3-butanediol, about 15 wt % of S,S-2,3-butanediol, about 70 wt % of meso-2,3-butanediol, hereinafter referred to as 2,3-butanediol. For absorption, 497 g/h of water were fed in recycle gas flow direction at a point directly upstream of the column head cooler of the absorption column. The recycle gas flow was adjusted such that the reactor reached a recycle gas flow of 5800 g/h in the stable state. The reactor was operated at $11*10^5$ Pa pressure and 180° C. coolant temperature.

Acid separation from the reaction gas was effected by absorption in a countercurrent absorber with structured packing, an inside diameter of 43 mm and a packing height of 3240 mm at a head temperature of 130° C. for the absorber.

A 2,3-butanediol and acetoin conversion of in each case 100% was achieved under these conditions. Acetic acid selectivity based on conversion was 81 mol % and formic acid selectivity based on conversion was 6.7 mol %. Volume-specific acetic acid productivity was about 600 g/lh. The crude acid contained 80 wt % of water.

EXAMPLE 20

Example 20 was carried out similarly to Example 19, except for the differences reported in Table 5.

TABLE 1

Oxidation of 2,3-butanediol with catalyst I:

|  | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| T (cool) ° C. | 180 | 199 | 194 | 176 | 173 | 167 | 199 | 190 | 178 |
| P (reac) bar (g) | 10.9 | 11 | 6 | 11 | 11 | 11 | 6.0 | 11 | 11 |
| Recycle gas flow [kg/h] | 7.0 | 7.3 | 3.7 | 7.1 | 7.1 | 6.7 | 3.7 | 7.3 | 7.3 |
| 2,3-Butanediol [g/h] | 97.9 | 97.9 | 97.1 | 125.3 | 149.5 | 97.1 | 123.5 | 98.8 | 124.2 |
| $H_2O$ feed [g/h] | 498 | 498 | 496.9 | 498.9 | 498.9 | 497.9 | 493.8 | 308.3 | 310.3 |
| Conversion [%] | 100 | 100 | 100 | 100 | 100 | 100 | 100 | 100 | 100 |
| Acetic acid selectivity [mol %] | 82 | 79 | 82 | 83 | 83 | 83 | 80 | 80 | 81 |
| Formic acid selectivity [mol %] | 6 | 4.5 | 4 | 5 | 5.6 | 6.3 | 2.3 | 4.6 | 5.6 |
| Acetic acid STY* [g/lh] | 453 | 435 | 450 | 581 | 686 | 454 | 560 | 438 | 558 |

STY: volume-specific productivity (space-time yield)

TABLE 2

Oxidation of acetoin with catalyst I:

|  | Ex. 10 | Ex. 11 | Ex. 12 | Ex. 13 | Ex. 14 |
|---|---|---|---|---|---|
| T (cool) ° C. | 208 | 214 | 195 | 222 | 187 |
| P (reac) bar (g) | 11 | 11 | 11 | 11 | 11 |
| Recycle gas flow [kg/h] | 6.95 | 6.9 | 6.4 | 6.4 | 6.3 |
| Acetoin [g/h] | 58 | 58 | 58 | 57 | 47 |
| $H_2O$ feed [g/h] | 218 | 218 | 218 | 218 | 218 |

TABLE 2-continued

Oxidation of acetoin with catalyst I:

|  | Ex. 10 | Ex. 11 | Ex. 12 | Ex. 13 | Ex. 14 |
|---|---|---|---|---|---|
| Conversion [%] | 100 | 100 | 100 | 100 | 100 |
| Acetic acid selectivity [mol %] | 80 | 79 | 83 | 73 | 86 |
| Formic acid selectivity [mol %] | 2.4 | 2.2 | 3.8 | 1.4 | 4.0 |
| Acetic acid STY [g/lh] | 270 | 265 | 278 | 235 | 235 |

TABLE 3

Oxidation of 2,3-butanediol with catalyst II:

|  | Ex. 15 | Ex. 16 |
|---|---|---|
| T (cool) ° C. | 243.5 | 234 |
| P (reac) bar (g) | 10.9 | 10.9 |
| Recycle gas flow [kg/h] | 6.0 | 5.93 |
| 2,3-Butanediol [g/h] | 105 | 104 |
| $H_2O$ feed [g/h] | 520 | 519 |
| Conversion [%] | 100 | 100 |
| Acetic acid selectivity [mol %] | 92 | 93 |
| Formic acid selectivity [mol %] | 1 | 1 |
| Acetic acid STY [g/lh] | 453 | 454 |

TABLE 4

Oxidation of 2,3-butanediol with catalyst III:

|  | Ex. 17 | Ex. 18 |
|---|---|---|
| T (cool) ° C. | 180 | 190.5 |
| P (reac) bar (g) | 11 | 11 |
| Recycle gas flow [kg/h] | 6 | 6 |
| 2,3-Butanediol [g/h] | 99.7 | 99.7 |
| $H_2O$ feed [g/h] | 497 | 497 |
| Conversion [%] | 100 | 100 |
| Acetic acid selectivity [mol %] | 84.5 | 82.7 |
| Formic acid selectivity [mol %] | 5.4 | 5.6 |
| Acetic acid STY [g/lh] | 600 | 590 |

TABLE 5

Oxidation of 2,3-butanediol/acetoin mixtures with catalyst III:

|  | Ex. 19 | Ex. 20 |
|---|---|---|
| T (cool) ° C. | 180 | 187 |
| P (reac) bar (g) | 11 | 11 |
| Recycle gas flow [kg/h] | 5.8 | 5.8 |
| 2,3-Butanediol [g/h] | 89.6 | 88.3 |
| Acetoin [g/h] | 10.0 | 9.8 |

TABLE 5-continued

Oxidation of 2,3-butanediol/acetoin mixtures with catalyst III:

|  | Ex. 19 | Ex. 20 |
|---|---|---|
| Water feed [g/h] | 497 | 496 |
| Conversion (2,3-BDO + acetoin) [%] | 100 | 100 |
| Acetic acid selectivity [mol %] | 81 | 82 |
| Formic acid selectivity [mol %] | 6.7 | 6.1 |
| Acetic acid STY [g/lh] | 600 | 600 |

The invention claimed is:

1. A method for producing a carboxylic acid having 1-3 carbon atoms, said method comprising the steps of:
   fermenting a carbohydrate-containing raw material to obtain a mixture containing as an intermediate at least one of 2,3-butanediol and acetoin; and
   oxidizing the intermediate to produce the carboxylic acid having 1-3 carbon atoms, wherein the oxidizing step is catalyzed by a vanadium-containing catalyst.

2. The method of claim 1, wherein the carboxylic acid having 1-3 carbon atoms is acetic acid.

3. The method of claim 1, wherein the oxidizing step is conducted in a presence of oxygen or an oxygen-containing gas in addition to the vanadium-containing catalyst.

4. The method of claim 1, wherein the oxidizing step is effected as heterogeneously catalyzed gas phase oxidation.

5. The method of claim 1, wherein the carbohydrate-containing raw material contains: (a) mono-, di- and oligosaccharides, and (b) at least one of C6 and C5 simple sugars.

6. The method of claim 1, wherein the carbohydrate-containing raw material contains: (a) at least one of sucrose and maltose, and (b) at least one of glucose, xylose and arabinose.

7. The method of claim 1, wherein the mixture is an aqueous solution having a water concentration of 1-90 wt %, and a collective fermentation byproduct concentration of less than 60 wt % based on a total amount of 2,3-butanediol and acetoin present in the aqueous solution, no individual fermentation byproduct being present in an amount of 30 wt % or more.

8. The method of claim 7, wherein the water concentration is 40-80 wt %.

9. The method of claim 1, wherein the oxidizing step is conducted at a reaction temperature of 100° C. to 400° C.

10. The method of claim 1, wherein the oxidizing step is conducted at a reaction temperature of 150° C. to 300° C.

11. The method of claim 1, wherein the oxidizing step is conducted at a reaction temperature of 180° C. to 290° C.

12. The method of claim 1, wherein the oxidizing step is conducted at a pressure from $1.2 \times 10^5$ to $51 \times 10^5$ Pa.

13. The method of claim 1, wherein the oxidizing step is conducted at a pressure from $3 \times 10^5$ to $21 \times 10^5$ Pa.

14. The method of claim 1, wherein the oxidizing step is conducted at a pressure from $4 \times 10^5$ to $12 \times 10^5$ Pa.

\* \* \* \* \*